United States Patent
Elsayed et al.

(10) Patent No.: US 10,875,006 B1
(45) Date of Patent: Dec. 29, 2020

(54) LUMINESCENT NANOCOMPOSITE FOR ULTRASENSITIVE DETECTION OF MERCURY

(71) Applicant: King Abdulaziz University, Jeddah (SA)

(72) Inventors: Waleed Elsayed Mahmoud Elsayed, Jeddah (SA); Ahmed Abdullah Salem Al-Ghamdi, Jeddah (SA); Yusef Abdulaziz Al-Turki, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 16/999,115

(22) Filed: Aug. 21, 2020

(51) Int. Cl.
| | | |
|---|---|---|
| *B01D 15/00* | (2006.01) | |
| *B01J 20/22* | (2006.01) | |
| *C02F 1/28* | (2006.01) | |
| *G01N 1/00* | (2006.01) | |
| *G01N 21/64* | (2006.01) | |
| *G01N 33/18* | (2006.01) | |
| *B01J 20/28* | (2006.01) | |
| *G01N 1/40* | (2006.01) | |
| *G01N 1/10* | (2006.01) | |
| *G01N 33/84* | (2006.01) | |
| *C02F 101/20* | (2006.01) | |

(52) U.S. Cl.
CPC ............ *B01J 20/223* (2013.01); *B01D 15/00* (2013.01); *B01J 20/28007* (2013.01); *B01J 20/28011* (2013.01); *C02F 1/288* (2013.01); *G01N 1/10* (2013.01); *G01N 1/405* (2013.01); *G01N 21/643* (2013.01); *G01N 33/1813* (2013.01); *G01N 33/84* (2013.01); *C02F 1/281* (2013.01); *C02F 1/285* (2013.01); *C02F 2101/20* (2013.01); *C02F 2305/08* (2013.01); *G01N 2021/6439* (2013.01)

(58) Field of Classification Search
CPC ................ B01J 20/223; B01J 20/28007; B01J 20/28011; B01D 15/00; C02F 1/288; C02F 1/281; C02F 1/285; C02F 2101/20; C02F 2305/08; G01N 1/10; G01N 1/405; G01N 21/643; G01N 33/1813; G01N 33/84; G01N 2021/6439
See application file for complete search history.

(56) References Cited

U.S. PATENT DOCUMENTS 9,422,473 B2    8/2016   Ebert

FOREIGN PATENT DOCUMENTS

| CN | 101195744 | 6/2008 |
|---|---|---|
| CN | 107142107 | 9/2017 |
| GB | 999564 | 7/1965 |
| WO | 2018220166 | 12/2018 |

OTHER PUBLICATIONS

Jiang et al., "Highly sensitive detection of mercury(II) ions with few-layer molybdenum disulfide", Nano Research 2015, 8(1): 257-262.

*Primary Examiner* — Dirk R Bass
(74) *Attorney, Agent, or Firm* — W&C IP (57) ABSTRACT

A luminescent nanocomposite is provided comprising nanosheets comprising a transition metal selected from the group consisting of molybdenum and tungsten; a chalcogen element; and a rare earth element; and a beta-lactam dye disposed upon a surface of the nanosheets. Methods of using the luminescent nanocomposite to detect and remove mercury (II) ions from a fluid sample are also provided.

13 Claims, 5 Drawing Sheets

LUMINESCENT NANOCOMPOSITE FOR ULTRASENSITIVE DETECTION OF MERCURY

FIELD OF THE INVENTION

The invention is generally related to a luminescent nanocomposite comprising nanosheets of a material having the formula $Mo_{1-x}Lu_xS_2$ and a beta-lactam dye and methods of detecting the presence of mercury (II) ions using the luminescent nanocomposite.

BACKGROUND OF THE INVENTION

The abatement of mercury from the aqueous environment has been of paramount concern because of its harmful effect on the health of human beings and on the aquatic ecology. Moreover, the advancement of various industries instigated a critical toxicity in water, where mercury is one of the most ubiquitous and dangerous heavy metals in the aqueous environment. Most of the mercury ions come from the discharge of industries, such as the cement industry, oil refineries, pulp industries, and plastic industries. The contamination of water with mercury and its various chemical forms causes serious harmful diseases such as skin and lung cancer, and kidney failure. Various techniques were developed to monitor the level of the mercury such as atomic emission spectrometry, inductive coupled plasma spectrometry, electrochemical technique and stripping chrono-potentiometric (SCP) method. Although these analytical techniques can detect mercury at low levels, it suffers from the interference by different elements during detection in addition to their high cost. Thus, there is a real need to develop low cost, highly sensitive and reliable techniques for accurate detection of mercury at very low levels below the permissible value mentioned by the world health organization which is around 10 ppm.

SUMMARY

The present disclosure provides a superior material that is able to monitor traces of mercury to avoid its harmful effect on humans, plants and animals. A luminescent nanocomposite is provided for the efficient detection of ultra-trace amounts of mercury. The fluoroprobe is made of quantum materials decorated with beta lactamase. A reduction in fluorescence intensity is indicative of the presence of mercury ions. The fluorescence probe has a high photostability against temperature and storage time.

An aspect of the disclosure provides a luminescent nanocomposite comprising nanosheets comprising a transition metal selected from the group consisting of molybdenum and tungsten; a chalcogen element; and a rare earth element; and β-Lactamase disposed upon a surface of the nanosheets. In some embodiments, the transition metal is molybdenum; the chalcogen element is sulfur; the rare earth element is lutetium; and the nanosheets have a chemical formula $Mo_{1-x}Lu_xS_2$, where $0.25 \leq x \leq 0.75$, e.g. 0.5.

In some embodiments, a weight ratio of the β-Lactamase to the nanosheets is 1:0.9 to 1:25. In some embodiments, the luminescent nanocomposite displays a photoluminescence emission maximum at 725 to 775 nm. In some embodiments, the nanosheets are crystalline by powder X-ray diffraction (PXRD) and crystallize in the hexagonal crystal system. In some embodiments, the nanosheets have a mean thickness of 2 to 10 nm and a mean diameter of 300 to 1000 nm.

Another aspect of the disclosure provides a method of detecting mercury (II) ions in a fluid sample, comprising contacting the fluid sample with a luminescent nanocomposite as described herein to form an analyte mixture; and measuring a photoluminescence emission profile of the analyte mixture to determine a presence or absence of mercury (II) ions in the fluid sample, wherein a reduction in intensity of a luminescence emission peak associated with the luminescent nanocomposite indicates the presence of mercury (II) ions in the fluid sample. In some embodiments, the fluid sample is a water or blood sample.

Another aspect of the disclosure provides a method of removing mercury (II) ions from a fluid sample, comprising contacting the fluid sample with a luminescent nanocomposite as described herein to form an analyte mixture, whereby mercury (II) ions adsorb onto the luminescent nanocomposite to form a loaded nanocomposite; and separating the loaded nanocomposite from the mixture, wherein a concentration of mercury (II) ions in the fluid sample after the contacting and separating is lower than an initial concentration of mercury (II) ions in the fluid sample. In some embodiments, the fluid sample is a water or blood sample.

DETAILED DESCRIPTION

Embodiments of the disclosure provide an efficient fluorescence probe for mercury detection and removal. The luminescent nanocomposites described herein have various applications for the detection and removal of mercury including in the petroleum, electricity, health, water and agriculture sectors. The luminescent nanocomposite is formed from nanosheets comprising a transition metal; a chalcogen element; and a rare earth element. A nanosheet is a two-dimensional nanostructure with a thickness ranging from 1 to 100 nm. In some embodiments, the nanosheet has a mean thickness of 2-10 nm and has a mean diameter of 300 to 1000 nm.

The transition metal may molybdenum or tungsten. The chalcogen element is selected from oxygen, sulfur, selenium, tellurium, and polonium. The rare earth element is selected from cerium, dysprosium, erbium, europium, gadolinium, holmium, lanthanum, lutetium, neodymium, praseodymium, promethium, samarium, scandium, terbium, thulium, ytterbium, and yttrium.

In some embodiments, the transition metal is molybdenum; the chalcogen element is sulfur; the rare earth element is lutetium; and the nanosheets have a chemical formula $Mo_{1-x}Lu_xS_2$, where $0.25 \leq x \leq 0.75$, e.g. 0.5 ($Mo_{0.5}Lu_{0.5}S_2$). In some embodiments, the molybdenum source is molybdenum tetrachloride or molybdenum pentachloride or molybdenum oxide dichloride. In some embodiments, the sulfur source is phenyl trifluoromethyl sulfide. In some embodiments, the concentration of lutetium dopant is 40-60 mol %, e.g. 50 mol %.

The nanocomposite further comprises an organic dye such as a β-lactam dye disposed on the surface of the nanosheets to detect mercury ions only and avoid interference with other ions. In some embodiments, the nanosheets are decorated with β-Lactamase ($C_{21}H_{17}N_3O_8S_3$). In some embodiments, the amount of β-Lactamase on the surface of the 2D-layered nanosheets is 1:0.9 to 1:25, e.g. 1:1.3 by weight ratio with respect to molybdenum source amount.

A nanocomposite as disclosed herein is stable in both acidic and alkaline medium, i.e. pH ranging from 1-12. The nanocomposite also demonstrates high photostability against temperatures of at least or up to 65° C., e.g. from 10-65° C. or higher and at storage times of at least or up to 15 months, e.g. from 1-15 months or more.

The nanocomposite may be used to detect the presence of or determine the concentration of mercury ions in all kinds of fluid samples along a range from 0.0001 ppb to 1000 ppm. Fluid samples include, but are not limited to, water and blood samples. Suitable water sources include ground water, tap water, waste water, rivers, wheel water, oceans, and sea water. Methods of detection include steps of contacting the fluid sample with a luminescent nanocomposite as described herein to form an analyte mixture; and measuring a photoluminescence emission profile of the analyte mixture to determine a presence or absence of mercury (II) ions in the fluid sample, wherein a reduction in intensity of a luminescence emission peak (e.g. in the region of 700-800 nm, e.g. 725-775 nm) associated with the luminescent nanocomposite indicates the presence of mercury (II) ions in the fluid sample.

Further embodiments of the disclosure provide methods for the fast removal of mercury (II) from fluid samples such as contaminated water using a nanocomposite as described herein. The methods comprise contacting the fluid sample with a luminescent nanocomposite as described herein to form an analyte mixture, whereby mercury (II) ions adsorb onto the luminescent nanocomposite to form a loaded nanocomposite; and separating the loaded nanocomposite from the mixture by filtration. The filtration process may be carried out using filter paper (e.g. Whatmann filter paper, pore size of 2 nm). A concentration of mercury (II) ions in the fluid sample after the contacting and separating is lower than an initial concentration of mercury (II) ions in the fluid sample.

The contacting steps described herein may be performed at ambient temperature for a period of 5-10 min, e.g. 4-7 min. In some embodiments, the amount of the nanocomposite used for the detection and removal of mercury is in the range of 50-100 mg.

In some embodiments, a method as described herein removes 100 ppm of mercury from tap water to less than the detection limit of ICP-AES without disturbing the pH of the water. In some embodiments, a method as described herein removes 50 ppm of mercury from wheel water to less than the detection limit of ICP-AES without disturbing pH of the water. In some embodiments, a method as described herein removes 5 ppm of mercury from river water to less than the detection limit of ICP-AES without disturbing pH of the water. In some embodiments, a method as described herein removes 0.1 ppm of mercury from waste water to less than the detection limit of ICP-AES without disturbing pH of the water.

Embodiments of the disclosure also include methods of preparing a luminescent nanocomposite as described herein, e.g. by a sonochemical method. In some embodiments, the method comprises steps of a) Dissolving molybdenum tetrachloride and lutetium nitrate in 40 ml of ethylene glycol to obtain a solution mixture with molar ratio of lutetium to molybdenum around 0.5:0.5 by molar ratio followed by sonication at sonic frequency of 40 MHz and temperature of 40° C.;

b) Adding 5 mL of phenyl trifluoromethyl sulfide (1 mmol) to the solution mixture obtained in step (a) and raising the temperature to 80° C. and followed by sonication for 70 min to obtain the 2D-layered $Mo_{0.5}Lu_{0.5}S_2$ nanosheets; and c) Adding the as-prepared 2D-layered $Mo_{0.5}Lu_{0.5}S_2$ nanosheets powder in step (b) into the β-Lactamase solution and refluxed at 60° C. for 45 min to obtain the desired 2D-layered $Mo_{0.5}Lu_{0.5}S_2$ nanosheets functionalized with β-Lactamase.

In some embodiments, the weight ratio of molybdenum tetrachloride to β-Lactamase is in the range of 1:1.2 to 1:1.3.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

Preparation of 2D-layered $Mo_{0.5}Lu_{0.5}S_2$ Nanosheets

Figure 1:
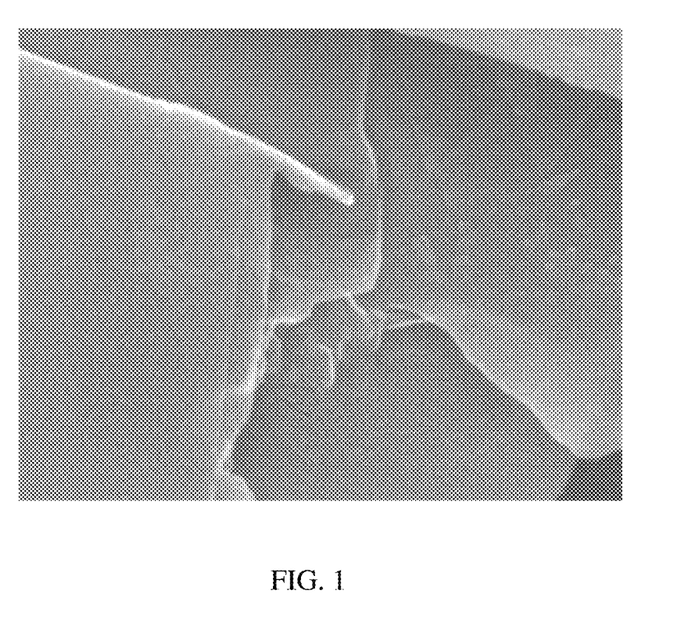
FIG. 1. A SEM image for the prepared 2D-layered $Mo_{0.5}Lu_{0.5}S_2$ nanosheets.
Figure 2:
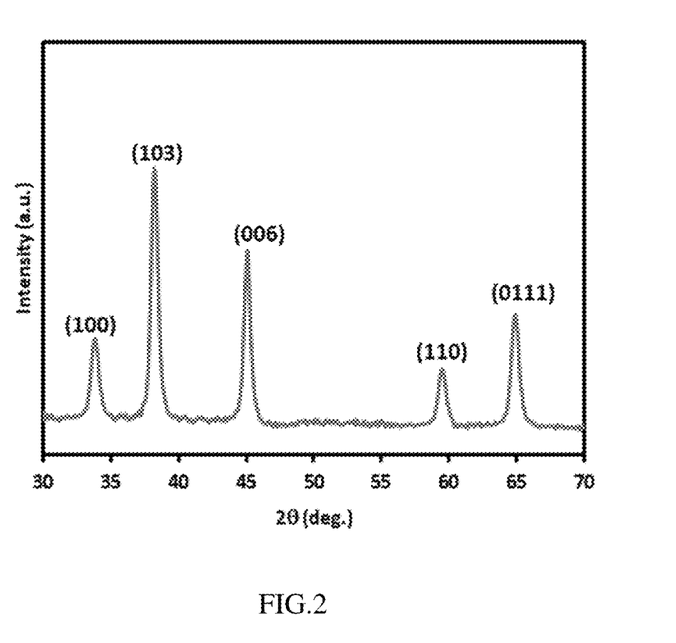
FIG. 2. The XRD patterns of the prepared $Mo_{0.5}Lu_{0.5}S_2$ nanosheets.

In a glass beaker, about 0.5 mmol of molybdenum tetrachloride and 0.5 mmol of lutetium nitrate are dissolved in 40 ml of ethylene glycol. The beaker was transferred to an ultrasonic bath adjusted at sonic frequency of 40 MHz and temperature of 40° C. Then, 5 mL of phenyl trifluoromethyl sulfide (1 mmol) was quickly injected. After injection, the temperature of the whole mixture was raised to 80° C. and kept sonicating for 70 min. After the reaction, the solution was left to cool down naturally and centrifuged at 12000 rpm for 10 min. The supernatant was collected and washed by isopropanol and action to remove the residue of ethylene glycol. The product was discarded and dried at 70° C. for 8 h. FIG. 1 shows the SEM image of the final product. It has a nanosheets like shape with a thickness of 5 nm and sheet length around 600 nm. FIG. 2 shows the XRD of the prepared 2D-layered $Mo_{0.5}Lu_{0.5}S_2$ nanosheets. All peaks are matched with the hexagonal phase of $MoS_2$ (JCPDS-Card no. 37-1492). There are no other peaks for Mo bi-products or lutetium or sulfur compounds in the XRD patterns, which indicate the dissolving of the lutetium atoms into the molybdenum sulfide crystal structure.

Example 2

Decoration of the 2D-Layered $Mo_{0.5}Lu_{0.5}S_2$ Nanosheets with β-Lactamase

Figure 3A:
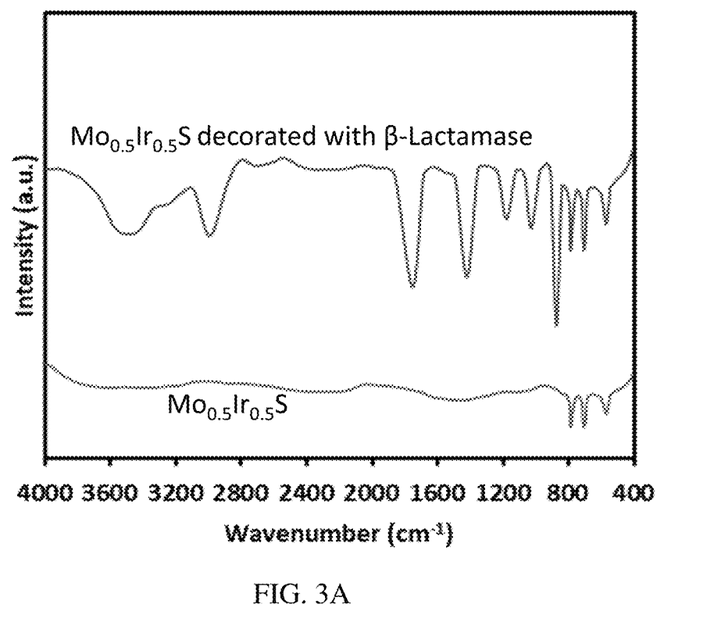
FIGS. 3A-B. (a) The FTIR spectra of the decorated 2D-layered $Mo_{0.5}Lu_{0.5}S_2$ nanosheets functionalized with β-Lactamase and (b) A schematic diagram for the mechanism of attachment of the β-Lactamase on the surface of the 2D-layered $Mo_{0.5}Lu_{0.5}S_2$ nanosheets.
Figure 3B:
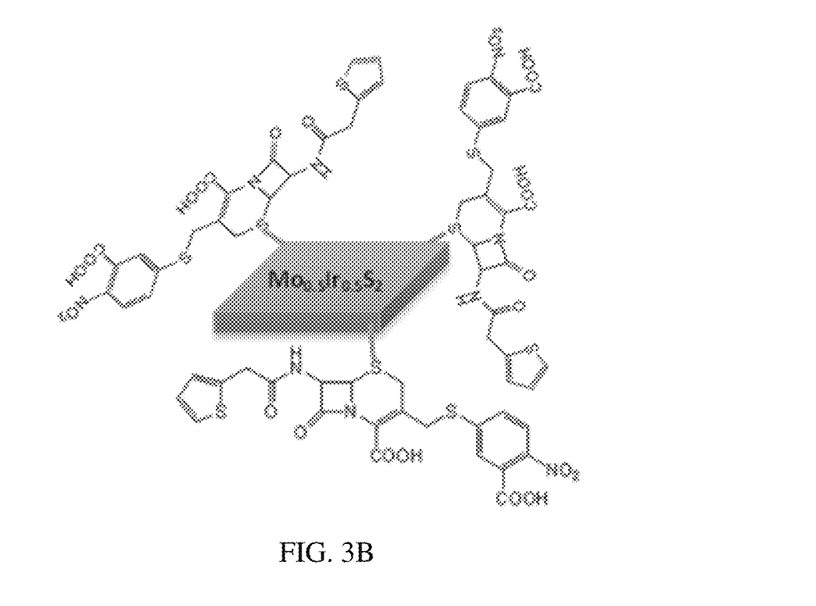

About 130 mg of the β-Lactamase is dissolved in 20 ml of isopropanol until a clear and homogenous solution was formed at 55° C. The as-prepared 2D-layered $Mo_{0.5}Lu_{0.5}S_2$ nanosheets (100 mg) was dispersed into the β-Lactamase solution and refluxed at 60° C. for 45 min. The product was collected through centrifuging at 12000 rpm for 8 min and left to dry under nitrogen flow. FIG. 3a depicts the FTIR spectra of the 2D-layered $Mo_{0.5}Lu_{0.5}S_2$ nanosheets before and after decoration with β-Lactamase. The 2D-layered $Mo_{0.5}Lu_{0.5}S_2$ nanosheets before decoration showed two bands at 579 $cm^{-1}$ and 471 $cm^{-1}$ which assigned to Mo—S and Mo—S—Lu bending. The IR spectra after decoration with β-Lactamase showed eight additional absorption bands located at 3504 $cm^{-1}$ 2998 $cm^{-1}$, 1632 $cm^{-1}$, 1418 $cm^{-1}$, 1187 $cm^{-1}$, 1046 $cm^{-1}$, 887 $cm^{-1}$ and 788 $cm^{-1}$ which correspond to N—H stretching, C—H stretching, S—C stretching, C—C stretching, N—O stretching and C—O bending, S—C—S bending, C—S—Mo bending vibrations, respectively. This implies that the β-Lactamase is attached to the surface of the 2D-layered $Mo_{0.5}Lu_{0.5}S_2$ nanosheets according to the mechanism shown in FIG. 3b.

Example 3

Figure 4:
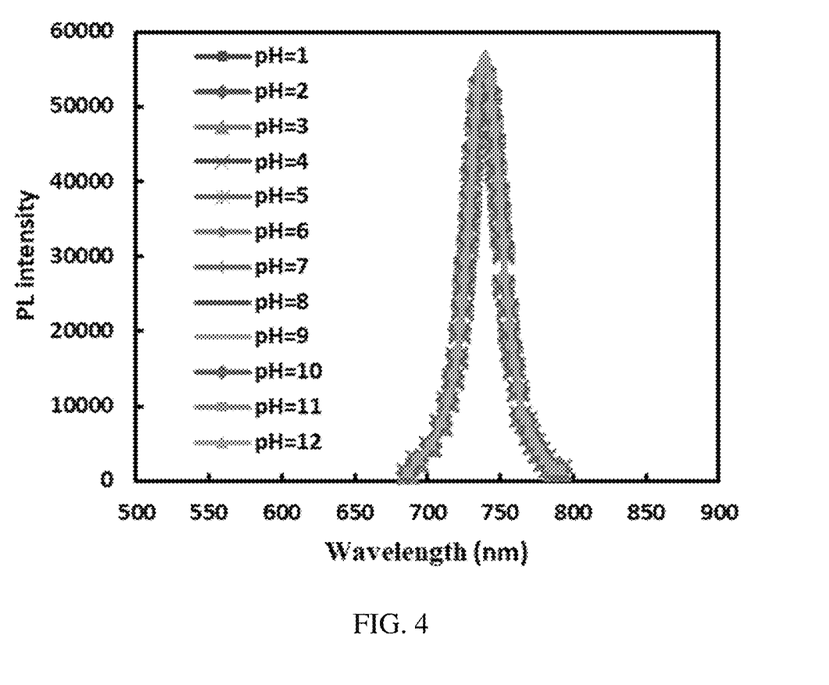
FIG. 4. The luminescence spectra of the decorated 2D-layered $Mo_{0.5}Lu_{0.5}S_2$ nanosheets with β-Lactamase at different pH values.

Photostability of the Decorated 2D-Layered $Mo_{0.5}Lu_{0.5}S_2$ Nanosheets Against pH A water soluble solution of the 2D-layered $Mo_{0.5}Lu_{0.5}S_2$ nanosheets decorated with β-Lactamase was prepared by dispersing 50 mg of the β-Lactamase decorated $Mo_{0.5}Lu_{0.5}S_2$ nanosheets in 10 ml of deionized water and sonicated for 25 min at room temperature. The pH value was determined by the pH meter and was found to be 7. Various solutions with different pH values were prepared by adding HCl and NaOH. Solutions with pH values from 1 to 6 was prepared by adding HCl (2M) from 1.4 ml to 0.06 ml. Solutions with pH values from 8 to 12 were prepared by adding NaOH (2M) from 0.1 to 1.2 ml to the water soluble β-Lactamase decorated $Mo_{0.5}Lu_{0.5}S_2$ nanosheets. The fluorescence intensity was measured by Perkin Elmer LS-55 Fluorescence Spectrometer. The width of the slit was adjusted at 1.4 nm at excitation wavelength of 430 nm. FIG. 4 shows the influence of the pH value on the luminescence intensity of the β-Lactamase decorated $Mo_{0.5}Lu_{0.5}S_2$ nanosheets. The luminescence intensity was around 53400±34 along the pH values from 1 to 12, implying that the developed β-Lactamase decorated $Mo_{0.5}Lu_{0.5}S_2$ nanosheets has high photostability in the acidic and alkaline media.

Example 4

Figure 5:
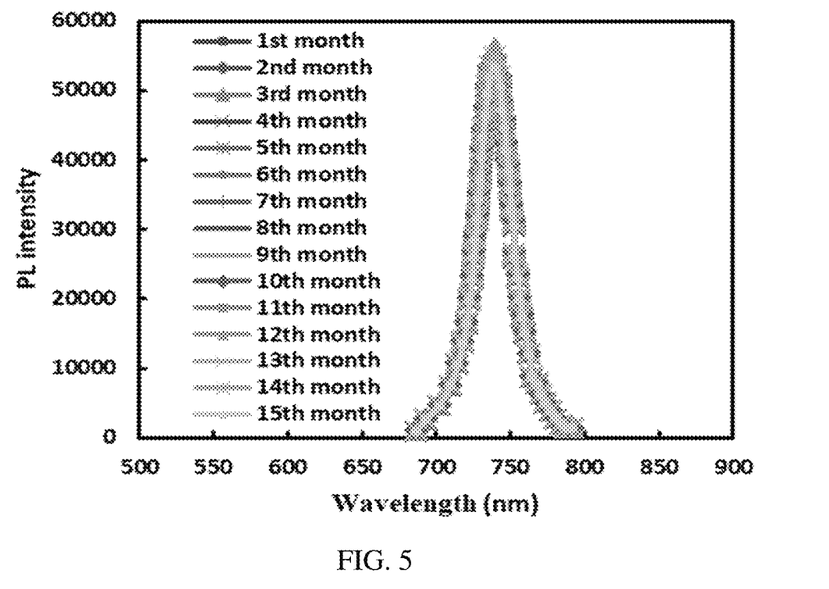
FIG. 5. The luminescence spectra of the decorated 2D-layered $Mo_{0.5}Lu_{0.5}S_2$ nanosheets with β-Lactamase at different storage times.

Photostability of the Decorated 2D-Layered $Mo_{0.5}Lu_{0.5}S_2$ Nanosheets Against Storage Time A water soluble solution of the β-Lactamase decorated $Mo_{0.5}Lu_{0.5}S_2$ nanosheets was prepared by dispersing 50 mg of the β-Lactamase decorated $Mo_{0.5}Lu_{0.5}S_2$ nanosheets in 10 ml of deionized water and sonicated for 25 min at room temperature. This solution is stored in refrigerator at 4° C. for 15 months. The luminescence spectra of this solution were measured along this period of time at the same conditions presented in example 3. FIG. 5 shows the influence of the storage time on the luminescence intensity of the β-Lactamase decorated $Mo_{0.5}Lu_{0.5}S_2$ nanosheets. The luminescence intensity was around 53400±34 along the time from 1 to 15 months, implying that the developed 53400±34 has high photostability against storage time.

Example 5

Figure 6:
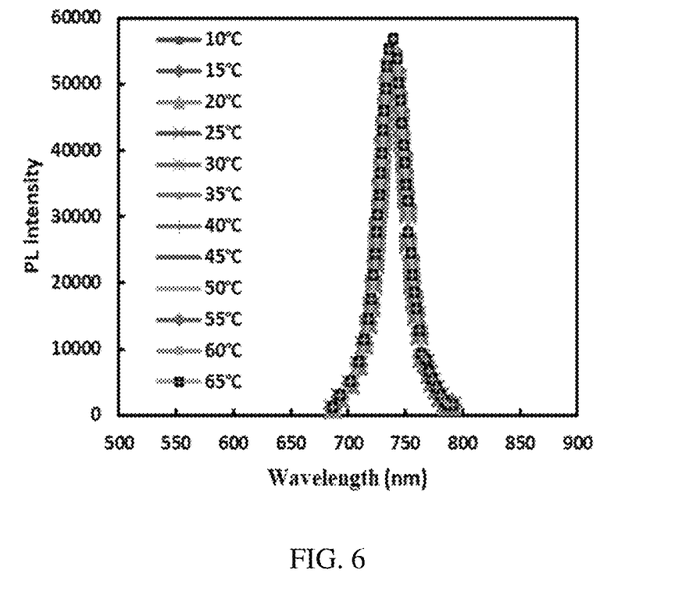
FIG. 6. The luminescence spectra of the decorated 2D-layered $Mo_{0.5}Lu_{0.5}S_2$ nanosheets with β-Lactamase at different temperatures.

Photostability of the Decorated 2D-Layered $Mo_{0.5}Lu_{0.5}S_2$ Nanosheets Against Temperature A water soluble solution of the β-Lactamase decorated $Mo_{0.5}Lu_{0.5}S_2$ nanosheets was prepared by dispersing 50 mg of the β-Lactamase decorated $Mo_{0.5}Lu_{0.5}S_2$ nanosheets in 10 ml of deionized water and sonicated for 7 min at room temperature. The temperature of this solution is raised to 65° C. The luminescence spectra of this solution were measured along the temperature range from 10° C. to 65° C. at the same conditions presented in example 3. FIG. 6 shows the influence of the temperature on the luminescence intensity of the β-Lactamase decorated $Mo_{0.5}Lu_{0.5}S_2$ nanosheets. The luminescence intensity was around 53400±34 along the temperature range from 10° C. to 65° C., implying that the β-Lactamase decorated $Mo_{0.5}Lu_{0.5}S_2$ nanosheets has high photostability against temperature.

Example 6

Preparation of Mercury (III) Solution in Water 1 mg of Mercury(II) perchlorate was dissolved in 1000 ml of deionized water to obtain mercury solution of 1000 ppm. This standard mercury solution was further diluted to get solutions of different concentrations of mercury reached to (0.001 ppb, 0.01 ppb, 0.1 ppb, 1 ppb, 10 ppb, 100 ppb, 1 ppm, 10 ppm and 100 ppm).

Example 7

Detection of Mercury (III) in Water

Figure 7A:
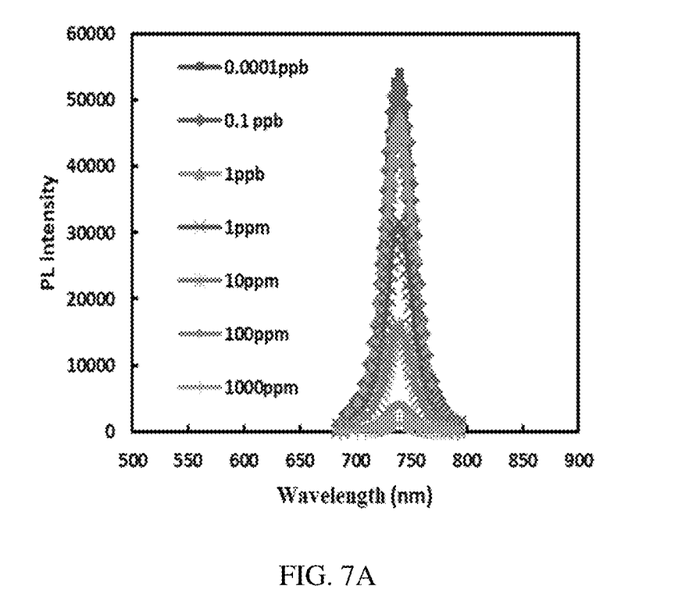
FIGS. 7A-B. (a) The luminescence spectra of the decorated 2D-layered $Mo_{0.5}Lu_{0.5}S_2$ nanosheets with β-Lactamase at different mercury concentrations in water and (b) the calibration curve of the relative luminescence intensity against mercury concentrations (inset: the calibration at low concentrations in the ppb range).
Figure 7B:
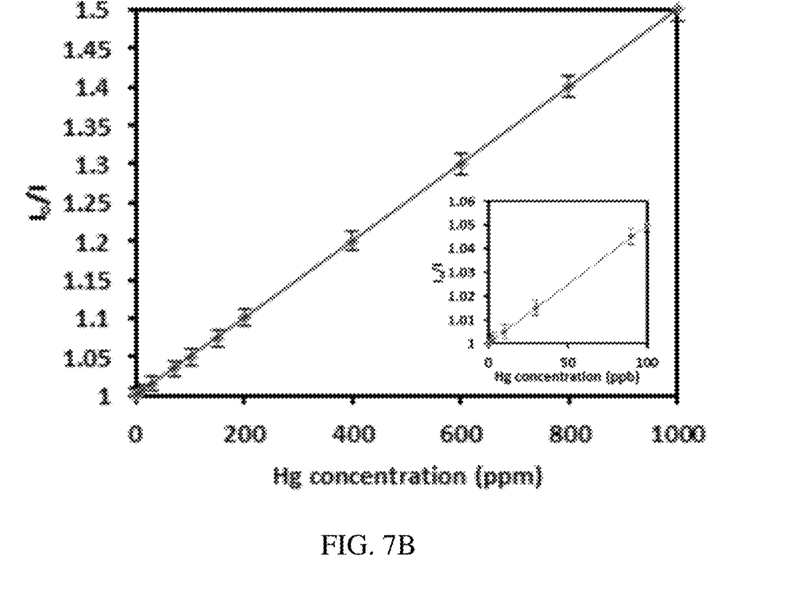

To each 10 ml of the contaminated water and blood serum with mercury with concentrations of 0.0001 ppb, 0.01 ppb, 0.1 ppb, 1 ppb, 1 ppm, 10 ppm, 100 ppm and 1000 ppm, 1 mg of the β-Lactamase decorated $Mo_{0.5}Lu_{0.5}S_2$ nanosheets are added and sonicated for 15 min at room temperature. The fluorescence intensity was measured by Perkin Elmer LS-55 Fluorescence Spectrometer. The width of the slit was adjusted at 1.4 nm at excitation wavelength of 430 nm. FIG. 7a shows the FL intensity of the β-Lactamase decorated $Mo_{0.5}Lu_{0.5}S_2$ nanosheets at various concentrations of mercury ions in water. It is clearly seen that the FL intensity of the β-Lactamase decorated $Mo_{0.5}Lu_{0.5}S_2$ nanosheets is decreased as the concentration of Hg(II) ions increased. FIG. 7b show the variation of the fluorescence intensity of the β-Lactamase decorated $Mo_{0.5}Lu_{0.5}S_2$ nanosheets as a function of the Hg(II) concentration in water. The FL intensity is linearly changed with the Hg(II) ions concentration along the range 0.001 ppb to 1000 ppm with linear correlation factor of $R^2=0.999$. The linear relationship was fitted by the Stern-Volmer relation, which defined as $$I_0/I = 1 + K_{SV}C \qquad (1)$$

where $I_o$ and $I_{As}$ are the FL intensity of the β-Lactamase decorated $Mo_{0.5}Lu_{0.5}S_2$ nanosheets in the absence and presence of mercury ions, respectively. K is Stern-Volmer constant and C is the mercury ions concentration. The Stern-Volmer relation fitted well the experimental data and the $K_{SV}$ was found about 0.05. The detection limit (3σ) was determined and it is about 0.0001 ppb.

Example 9

Detection of Mercury (II) in the Presence of Foreign Ions

Figure 8:
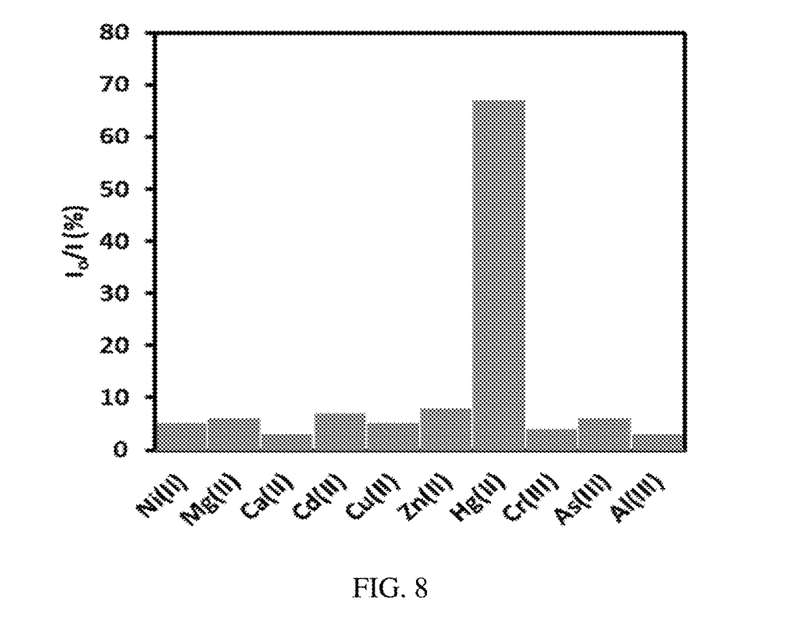
FIG. 8. The plot of the relative intensity of decorated 2D-layered $Mo_{0.5}Lu_{0.5}S_2$ nanosheets with β-Lactamase in the presence of different metal ions at concentration of 100 ppm.

Since the practical application of the fluorescence probe mainly depends on its high selectivity of the target ions, the influence of the abundant foreign ions in nature on the β-Lactamase decorated $Mo_{0.5}Lu_{0.5}S_2$ nanosheets was investigated. FIG. 8 depicts the effect of some selected foreign ions on the FL intensity of the β-Lactamase decorated $Mo_{0.5}Lu_{0.5}S_2$ nanosheets. The $Ni^{2+}$, $Mg^{2+}$, $Ca^{2+}$, $Cd^{2+}$, $Cu^{2+}$, $Zn^{2+}$, $Cr^{3+}$, $As^{3+}$ and $Al^{3+}$ ions showed negligible effect compared to the $Hg^{2+}$ ions at the same concentration (1000 ppm). However, the standard deviation of 50 measurements of the FL intensity in the presence of 10 ppb of Hg and 100 ppb of the foreign ions was about 1.003%. The introduction of the foreign ions with different ratios (1:10, 1:100, 1:1000, 1:10000 and 1:100000) showed interference less than 1.003%.

Example 10

Adsorption of Mercury (II) on the Surface of the β-Lactamase Decorated $Mo_{0.5}Lu_{0.5}S_2$ Nanosheets To determine the amount of mercury adsorbed by the β-Lactamase decorated $Mo_{0.5}Lu_{0.5}S_2$ nanosheets inductively coupled plasma mass spectroscopy was performed for the contaminated water and blood serum by mercury before and after the adsorption process. Various contaminated samples were firstly prepared in tap water (contains 100 ppm of Hg), wheel water (contains 50 ppm of Hg), river water (contains 5 ppm of Hg), and waste water (contains 0.1 ppm of Hg). To each 10 ml of solution, 1 mg of the β-Lactamase decorated $Mo_{0.5}Lu_{0.5}S_2$ nanosheets was added and sonicated for 15 min. Then the β-Lactamase decorated $Mo_{0.5}Lu_{0.5}S_2$ nanosheets powder was collected by centrifuging at 12000 rpm and left to dry naturally at ambient conditions. The ICP-AES analysis for the collected β-Lactamase decorated $Mo_{0.5}Lu_{0.5}S_2$ nanosheets powder and the solutions after adsorption process were performed and the results presented in Table 1. This table shows that the mercury is adsorbed by the β-Lactamase decorated $Mo_{0.5}Lu_{0.5}S_2$ nanosheets. This analysis supports the interaction of mercury with the β-Lactamase decorated $Mo_{0.5}Lu_{0.5}S_2$ nanosheets and demonstrates that the probe could remove the mercury from the solutions efficiently.

TABLE 1

| Sample | Amount of Hg in the sample (ppm) | Amount of Hg adsorbed on the surface of decorated 2D-layerd $Mo_{0.5}Lu_{0.5}S_2$ nanosheets functionalized with β-Lactamase (ppm) | Amount of Hg in the sample after adsorption process (ppm) | Rate of removal (%) |
|---|---|---|---|---|
| Tap water | 100 | 99.9999 | Below detection limit | 99.9999 |
| Wheel water | 50 | 49.9991 | Below detection limit | 99.9998 |
| River water | 5 | 4.9998 | Below detection limit | 99.9997 |
| Waste water | 0.1 | 0.0999 | Below detection limit | 99.9999 |

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A luminescent nanocomposite comprising:
Nanosheets comprising
   A transition metal selected from the group consisting of molybdenum and tungsten;
   A chalcogen element;
   A rare earth element; and
β-Lactamase disposed upon a surface of the nanosheets.

2. The luminescent nanocomposite of claim 1, wherein:
the transition metal is molybdenum;
the chalcogen element is sulfur;
the rare earth element is lutetium; and
the nanosheets have a chemical formula $Mo_{1-x}Lu_xS_2$, where $0.25 \leq x \leq 0.75$.

3. The luminescent nanocomposite of claim 2, wherein x is 0.5.

4. The luminescent nanocomposite of claim 1, wherein a weight ratio of the β-Lactamase to the nanosheets is 1:0.9 to 1:25.

5. The luminescent nanocomposite of claim 1, wherein the luminescent nanocomposite displays a photoluminescence emission maximum at 725 to 775 nm.

6. The luminescent nanocomposite of claim 1, wherein the nanosheets are crystalline by powder X-ray diffraction (PXRD) and crystallize in the hexagonal crystal system.

7. The luminescent nanocomposite of claim 1, wherein the nanosheets have a mean thickness of 2 to 10 nm and a mean diameter of 300 to 1000 nm.

8. A method of detecting mercury (II) ions in a fluid sample, comprising:
contacting the fluid sample with the luminescent nanocomposite of claim 1 to form an analyte mixture; and
measuring a photoluminescence emission profile of the analyte mixture to determine a presence or absence of mercury (II) ions in the fluid sample,
wherein a reduction in intensity of a luminescence emission peak associated with the luminescent nanocomposite indicates the presence of mercury (II) ions in the fluid sample.

9. The method of claim 8, wherein the fluid sample is a water sample.

10. The method of claim 8, wherein the fluid sample is a blood sample.

11. A method of removing mercury (II) ions from a fluid sample, comprising:
contacting the fluid sample with the luminescent nanocomposite of claim 1 to form an analyte mixture, whereby mercury (II) ions adsorb onto the luminescent nanocomposite to form a loaded nanocomposite; and
separating the loaded nanocomposite from the mixture,
wherein a concentration of mercury (II) ions in the fluid sample after the contacting and separating is lower than an initial concentration of mercury (II) ions in the fluid sample.

12. The method of claim 11, wherein the fluid sample is a water sample.

13. The method of claim 11, wherein the fluid sample is a blood sample.

* * * * *